US012788300B2

(12) United States Patent
Holub

(10) Patent No.: US 12,788,300 B2
(45) Date of Patent: Nov. 10, 2026

(54) SYSTEMS AND METHODS OF SYNCHRONIZING EEG DATA WITH A PATIENT'S ASSOCIATED AUDIO AND VIDEO DATA

(71) Applicant: Cadwell Laboratories, Inc., Kennewick, WA (US)

(72) Inventor: Michal Holub, Block (SG)

(73) Assignee: Cadwell Laboratories, Inc., Kennewick, WA (US)

( * ) Notice: Subject to any disclaimer, the term of this patent is extended or adjusted under 35 U.S.C. 154(b) by 234 days.

(21) Appl. No.: 18/617,937

(22) Filed: Mar. 27, 2024

(65) Prior Publication Data

US 2024/0324934 A1 Oct. 3, 2024

Related U.S. Application Data

(60) Provisional application No. 63/492,893, filed on Mar. 29, 2023.

(51) Int. Cl.

| | |
|---|---|
| ***A61B 5/31*** | (2021.01) |
| ***A61B 5/00*** | (2006.01) |
| ***A61B 5/369*** | (2021.01) |

(52) U.S. Cl.

CPC ................ *A61B 5/31* (2021.01); *A61B 5/369* (2021.01); *A61B 5/4094* (2013.01)

(58) Field of Classification Search

CPC ......... A61B 5/31; A61B 5/369; A61B 5/4094; A61B 5/0077; A61B 5/384; A61B 5/7285; A61B 5/0033

See application file for complete search history.

(56) References Cited

U.S. PATENT DOCUMENTS

| | | | |
|---|---|---|---|
| 751,475 A | | 2/1904 | De Vilbiss |
| 2,320,709 A | | 6/1943 | Arnesen |

(Continued)

FOREIGN PATENT DOCUMENTS

| | | | |
|---|---|---|---|
| CN | 104766176 A | | 7/2015 |
| CN | 110753261 A | † | 2/2020 |

(Continued)

OTHER PUBLICATIONS

A. Ameera et al.; "Analysis of EEG Spectrum Bands Using Power Spectral Density for Pleasure and Displeasure State" 2019 IOP Conf. Ser.: Mater. Sci. Eng. 557 012030 (Year: 2019).*

(Continued)

*Primary Examiner* — Lynsey C Eiseman
*Assistant Examiner* — Christopher J Mutchler
(74) *Attorney, Agent, or Firm* — Novel IP

(57) ABSTRACT

Systems and methods of enabling synchronization of a patient's EEG data with associated video and audio data for analysis in a computing device include a synchronization device which generates, synchronously, first data indicative of a first differential electrical signal, second data indicative of a second differential electrical signal, a plurality of visible light signals that are acquired by a video acquisition device to generate third data and a plurality of audio signals that are acquired by an audio acquisition device to generate fourth data. The computing device compares the first data with the third data to calculate a first time compensation, compares the second data with the fourth data to calculate a second time compensation and applies the first compensation time to the patient's video data and the second compensation time to the patient's audio data.

17 Claims, 5 Drawing Sheets

(56) References Cited

U.S. PATENT DOCUMENTS

| | | | |
|---|---|---|---|
| 2,807,259 | A | 9/1957 | Guerriero |
| 2,950,437 | A | 8/1960 | Stahl |
| 3,165,340 | A | 1/1965 | Kuehl |
| 3,659,250 | A | 4/1972 | Horton |
| 3,682,162 | A | 8/1972 | Colyer |
| 3,985,125 | A | 10/1976 | Rose |
| 3,993,859 | A | 11/1976 | Mcneel |
| 4,155,353 | A | 5/1979 | Rea |
| 4,262,306 | A | 4/1981 | Renner |
| 4,263,899 | A | 4/1981 | Burgin |
| 4,545,374 | A | 10/1985 | Jacobson |
| 4,562,832 | A | 1/1986 | Wilder |
| 4,616,635 | A | 10/1986 | Caspar |
| 4,705,049 | A | 11/1987 | John |
| 4,716,901 | A | 1/1988 | Jackson |
| 4,743,959 | A | 5/1988 | Frederiksen |
| 4,765,311 | A | 8/1988 | Kulik |
| 4,817,587 | A | 4/1989 | Janese |
| 4,862,891 | A | 9/1989 | Smith |
| 4,889,502 | A | 12/1989 | Althouse |
| 4,914,508 | A | 4/1990 | Music |
| 5,107,845 | A | 4/1992 | Guern |
| 5,171,279 | A | 12/1992 | Mathews |
| 5,196,015 | A | 3/1993 | Neubardt |
| 5,284,153 | A | 2/1994 | Raymond |
| 5,284,154 | A | 2/1994 | Raymond |
| 5,299,563 | A | 4/1994 | Seton |
| 5,377,667 | A | 1/1995 | Patton |
| 5,438,989 | A | 8/1995 | Hochman |
| 5,462,448 | A | 10/1995 | Kida |
| 5,472,426 | A | 12/1995 | Bonati |
| 5,474,558 | A | 12/1995 | Neubardt |
| 5,540,235 | A | 7/1996 | Wilson |
| 5,544,286 | A | 8/1996 | Laney |
| 5,560,372 | A | 10/1996 | Cory |
| 5,565,779 | A | 10/1996 | Arakawa |
| 5,578,060 | A | 11/1996 | Pohl |
| 5,601,608 | A | 2/1997 | Mouchawar |
| 5,602,585 | A | 2/1997 | Dickinson |
| 5,625,759 | A | 4/1997 | Freeman |
| 5,648,815 | A | 7/1997 | Toba |
| 5,664,029 | A | 9/1997 | Callahan |
| 5,681,265 | A | 10/1997 | Maeda |
| 5,684,887 | A | 11/1997 | Lee |
| 5,728,046 | A | 3/1998 | Mayer |
| 5,741,261 | A | 4/1998 | Moskovitz |
| 5,766,133 | A | 6/1998 | Faisandier |
| 5,772,661 | A | 6/1998 | Michelson |
| 5,775,331 | A | 7/1998 | Raymond |
| 5,775,931 | A | 7/1998 | Jones |
| 5,785,648 | A | 7/1998 | Min |
| 5,792,044 | A | 8/1998 | Foley |
| 5,795,291 | A | 8/1998 | Koros |
| 5,830,150 | A | 11/1998 | Palmer |
| 5,847,755 | A | 12/1998 | Wixson |
| 5,860,973 | A | 1/1999 | Michelson |
| 5,868,668 | A | 2/1999 | Weiss |
| 5,885,210 | A | 3/1999 | Cox |
| 5,891,147 | A | 4/1999 | Moskovitz |
| 5,928,139 | A | 7/1999 | Koros |
| 5,928,158 | A | 7/1999 | Aristides |
| 5,930,379 | A | 7/1999 | Rehg |
| 5,931,777 | A | 8/1999 | Sava |
| 5,933,929 | A | 8/1999 | Kawakami |
| 5,944,658 | A | 8/1999 | Koros |
| 5,954,635 | A | 9/1999 | Foley |
| 5,993,385 | A | 11/1999 | Johnston |
| 6,004,312 | A | 12/1999 | Finneran |
| 6,004,341 | A | 12/1999 | Zhu |
| 6,026,180 | A | 2/2000 | Wittenstein |
| 6,042,540 | A | 3/2000 | Johnston |
| 6,062,216 | A | 5/2000 | Corn |
| 6,074,343 | A | 6/2000 | Nathanson |
| 6,088,878 | A | 7/2000 | Antonucci |
| 6,095,987 | A | 8/2000 | Shmulewitz |
| 6,109,948 | A | 8/2000 | Kuo |
| 6,116,941 | A | 9/2000 | Kuo |
| 6,119,306 | A | 9/2000 | Antonucci |
| 6,139,493 | A | 10/2000 | Koros |
| 6,152,871 | A | 11/2000 | Foley |
| 6,181,961 | B1 | 1/2001 | Prass |
| 6,196,969 | B1 | 3/2001 | Bester |
| 6,200,331 | B1 | 3/2001 | Swartz |
| 6,206,826 | B1 | 3/2001 | Mathews |
| 6,210,202 | B1 | 4/2001 | Kuo |
| 6,224,545 | B1 | 5/2001 | Cocchia |
| 6,236,874 | B1 | 5/2001 | Devlin |
| 6,241,548 | B1 | 6/2001 | Kuo |
| 6,259,945 | B1 | 7/2001 | Epstein |
| 6,264,491 | B1 | 7/2001 | Lord |
| 6,266,558 | B1 | 7/2001 | Gozani |
| 6,273,740 | B1 | 8/2001 | Lord |
| 6,287,322 | B1 | 9/2001 | Zhu |
| 6,302,842 | B1 | 10/2001 | Auerbach |
| 6,306,100 | B1 | 10/2001 | Prass |
| 6,309,349 | B1 | 10/2001 | Bertolero |
| 6,325,764 | B1 | 12/2001 | Griffith |
| 6,334,068 | B1 | 12/2001 | Hacker |
| 6,373,890 | B1 | 4/2002 | Freeman |
| 6,425,859 | B1 | 7/2002 | Foley |
| 6,450,952 | B1 | 9/2002 | Rioux |
| 6,466,817 | B1 | 10/2002 | Kaula |
| 6,473,639 | B1 | 10/2002 | Fischell |
| 6,500,128 | B2 | 12/2002 | Marino |
| 6,535,759 | B1 | 3/2003 | Epstein |
| 6,579,114 | B2 | 6/2003 | Lord |
| 6,609,018 | B2 | 8/2003 | Cory |
| 6,712,795 | B1 | 3/2004 | Cohen |
| 6,799,931 | B2 | 10/2004 | Kwilosz |
| 6,805,668 | B1 | 10/2004 | Cadwell |
| 6,837,716 | B1 | 1/2005 | Brazas |
| 6,847,849 | B2 | 1/2005 | Mamo |
| 6,851,430 | B2 | 2/2005 | Tsou |
| 6,869,301 | B2 | 3/2005 | Shimizu |
| 6,870,109 | B1 | 3/2005 | Villarreal |
| 6,926,728 | B2 | 8/2005 | Zucherman |
| 6,945,933 | B2 | 9/2005 | Branch |
| 7,072,521 | B1 | 7/2006 | Cadwell |
| 7,089,059 | B1 | 8/2006 | Pless |
| 7,104,965 | B1 | 9/2006 | Jiang |
| 7,177,677 | B2 | 2/2007 | Kaula |
| 7,214,197 | B2 | 5/2007 | Prass |
| 7,230,688 | B1 | 6/2007 | Villarreal |
| 7,261,688 | B2 | 8/2007 | Smith |
| 7,374,448 | B2 | 5/2008 | Jepsen |
| 7,470,236 | B1 | 12/2008 | Kelleher |
| 7,522,953 | B2 | 4/2009 | Kaula |
| 7,713,210 | B2 | 5/2010 | Byrd |
| 7,801,601 | B2 | 9/2010 | Maschino |
| 7,914,350 | B1 | 3/2011 | Bozich |
| 7,963,927 | B2 | 6/2011 | Kelleher |
| 7,983,761 | B2 | 7/2011 | Giuntoli |
| 8,108,039 | B2 | 1/2012 | Saliga |
| 8,147,421 | B2 | 4/2012 | Farquhar |
| 8,160,694 | B2 | 4/2012 | Salmon |
| 8,192,437 | B2 | 6/2012 | Simonson |
| D670,656 | S | 11/2012 | Jepsen |
| 8,323,208 | B2 | 12/2012 | Davis |
| 8,439,703 | B2 | 5/2013 | Natoli |
| 8,876,813 | B2 | 11/2014 | Min |
| 8,942,797 | B2 | 1/2015 | Bartol |
| 8,958,869 | B2 | 2/2015 | Kelleher |
| 9,084,551 | B2 | 7/2015 | Brunnett |
| 9,138,586 | B2 | 9/2015 | Eiger |
| 9,155,503 | B2 | 10/2015 | Cadwell |
| 9,295,401 | B2 | 3/2016 | Cadwell |
| 9,352,153 | B2 | 5/2016 | Van Dijk |
| 9,730,634 | B2 | 8/2017 | Cadwell |
| 10,238,467 | B2 | 3/2019 | Cadwell |
| 2001/0049510 | A1 | 12/2001 | Burr |
| 2002/0007188 | A1 | 1/2002 | Arambula |
| 2002/0009916 | A1 | 1/2002 | Lord |
| 2002/0088098 | A1 | 7/2002 | Bouley |
| 2002/0095080 | A1 | 7/2002 | Cory |

(56) References Cited

U.S. PATENT DOCUMENTS

2003/0045808 A1 3/2003 Kaula
2003/0074033 A1 4/2003 Pless
2004/0030258 A1 2/2004 Williams
2004/0127810 A1 7/2004 Sackellares
2004/0192100 A1 9/2004 Shimizu
2005/0003682 A1 1/2005 Brazas
2005/0075578 A1 4/2005 Gharib
2005/0085743 A1 4/2005 Hacker
2005/0148927 A1 7/2005 Ludin
2005/0182454 A1 8/2005 Gharib
2005/0182456 A1 8/2005 Ziobro
2005/0277844 A1 12/2005 Strother
2006/0009754 A1 1/2006 Boese
2006/0085048 A1 4/2006 Cory
2006/0085049 A1 4/2006 Cory
2006/0122514 A1 6/2006 Byrd
2006/0135877 A1 6/2006 Giftakis
2006/0258951 A1 11/2006 Bleich
2006/0276720 A1 12/2006 Mcginnis
2007/0016097 A1 1/2007 Farquhar
2007/0021682 A1 1/2007 Gharib
2007/0032841 A1 2/2007 Urmey
2007/0046471 A1 3/2007 Nyalamadugu
2007/0049962 A1 3/2007 Marino
2007/0184422 A1 8/2007 Takahashi
2007/0202005 A1 8/2007 Maschke
2008/0027507 A1 1/2008 Bijelic
2008/0058606 A1 3/2008 Miles
2008/0065144 A1 3/2008 Marino
2008/0071191 A1 3/2008 Kelleher
2008/0082136 A1 4/2008 Gaudiani
2008/0097164 A1 4/2008 Miles
2008/0108244 A1 5/2008 Jepsen
2008/0167574 A1 7/2008 Farquhar
2008/0183096 A1 7/2008 Snyder
2008/0194970 A1 8/2008 Steers
2008/0269777 A1 10/2008 Appenrodt
2008/0281313 A1 11/2008 Fagin
2008/0312520 A1 12/2008 Rowlandson
2009/0018399 A1 1/2009 Martinelli
2009/0043221 A1 2/2009 Kaplan
2009/0088660 A1 4/2009 Mcmorrow
2009/0105604 A1 4/2009 Bertagnoli
2009/0177112 A1 7/2009 Gharib
2009/0196471 A1 8/2009 Goetz
2009/0204016 A1 8/2009 Gharib
2009/0209879 A1 8/2009 Kaula
2009/0259108 A1 10/2009 Miles
2009/0279767 A1 11/2009 Kukuk
2010/0036384 A1 2/2010 Gorek
2010/0106011 A1 4/2010 Byrd
2010/0113898 A1 5/2010 Kim
2010/0152604 A1 6/2010 Kaula
2010/0168603 A1 7/2010 Himes
2010/0191305 A1 7/2010 Imran
2010/0249638 A1 9/2010 Liley
2010/0286554 A1 11/2010 Davis
2010/0317931 A1 12/2010 Sarkela
2010/0317989 A1 12/2010 Gharib
2011/0082383 A1 4/2011 Cory
2011/0184308 A1 7/2011 Kaula
2011/0295579 A1 12/2011 Tang
2011/0313530 A1 12/2011 Gharib
2012/0003862 A1 1/2012 Newman
2012/0046531 A1 2/2012 Hua
2012/0071779 A1 3/2012 Sarkela
2012/0109000 A1 5/2012 Kaula
2012/0109004 A1 5/2012 Cadwell
2012/0209082 A1 8/2012 Al-Ali
2012/0209346 A1 8/2012 Bikson
2012/0220891 A1 8/2012 Kaula
2012/0238855 A1 9/2012 Lanning
2012/0238893 A1 9/2012 Farquhar
2012/0265040 A1 10/2012 Ito
2012/0296230 A1 11/2012 Davis
2013/0012880 A1 1/2013 Blomquist
2013/0109996 A1 5/2013 Turnbull
2013/0138010 A1 5/2013 Nierenberg
2013/0152657 A1 6/2013 Swinehart
2013/0204315 A1 8/2013 Wongsarnpigoon
2013/0245463 A1 9/2013 Stuebe
2013/0253447 A1 9/2013 Ball
2013/0253611 A1 9/2013 Lee
2013/0303933 A1 11/2013 Bonnstetter
2013/0304407 A1 11/2013 George
2014/0121555 A1 5/2014 Scott
2014/0275926 A1 9/2014 Scott
2014/0276181 A1 9/2014 Sun
2014/0276925 A1 9/2014 Alves
2015/0150512 A1 6/2015 Warner
2015/0227702 A1 8/2015 Krishna
2015/0230749 A1 8/2015 Gharib
2015/0238106 A1 8/2015 Lappalainen
2015/0351643 A1 12/2015 Edwards
2015/0372433 A1 12/2015 Lisogurski
2016/0000382 A1 1/2016 Jain
2016/0174861 A1 6/2016 Cadwell
2016/0270679 A1 9/2016 Mahon
2016/0328991 A1 11/2016 Simpson
2017/0056663 A1 3/2017 Kaemmerer
2017/0100047 A1 4/2017 Edwards
2018/0117309 A1 5/2018 Rapoport
2018/0140829 A1 5/2018 Ramos De Miguel, Sr.
2018/0161123 A1 6/2018 Cadwell
2018/0198218 A1 7/2018 Regan
2018/0239430 A1* 8/2018 Tadi ........................ G06F 3/015
2018/0256097 A1 9/2018 Bray
2018/0296277 A1 10/2018 Schwartz
2019/0190187 A1 6/2019 Fukazawa
2020/0022603 A1 1/2020 Cardenas
2020/0108246 A1 4/2020 Cadwell
2020/0297282 A1 9/2020 Batzer
2020/0330772 A1 10/2020 Hartmann-Bax

FOREIGN PATENT DOCUMENTS

CN 111631703 A † 9/2020
DE 102014008684 A1 1/2016
EP 298268 1/1989
EP 0863719 A1 9/1998
EP 890341 1/1999
EP 972538 1/2000
EP 1182965 B1 3/2002
EP 2173238 A2 4/2010
JP H11513592 A 11/1999
JP 2008546509 A 12/2008
WO 2000038574 A1 7/2000
WO 2000066217 A1 11/2000
WO 2001037728 A1 5/2001
WO 2003005887 A2 1/2003
WO 2005030318 A1 4/2005
WO 2006042241 A2 4/2006
WO 2016028822 A1 2/2016
WO 2016105571 A1 6/2016

OTHER PUBLICATIONS

Aage R. Møller, "Intraoperative Neurophysiologic Monitoring", University of Pittsburgh, School of Medicine Pennsylvania, © 1995 by Harwood Academic Publishers GmbH.
Clements, et. al., "Evoked and Spontaneous Electromyography to Evaluate Lumbosacral Pedicle Screw Placement", 21 (5):600-604 (1996).
Danesh-Clough, et. al., "The Use of Evoked EMG in Detecting Misplaced Thoracolumbar Pedicle Screws", 26(12):1313-1316 (2001).
Dezawa et al., "Retroperitoneal Laparoscopic Lateral Approach to the Lumbar Spine: A New Approach, Technique, and Clinical Trial", Journal of Spinal Disorders 13(2):138-143 (2000).
Dickman, et al., "Techniques in Neurosurgery", National Library of Medicine, 3 (4) 301-307 (1997).
Epstein, et al., "Evaluation of Intraoperative Somatosensory-Evoked Potential Monitoring During 100 Cervical Operations",

(56) References Cited

OTHER PUBLICATIONS

18(6):737-747 (1993), J.B. Lippincott Company.
Glassman, et. al., "A Prospective Analysis of Intraoperative Electromyographic Monitoring of Pedicle Screw Placement with Computed Tomographic Scan Confirmation", 20(12):1375-1379.
Goldstein, et. al., "Minimally Invasive Endoscopic Surgery of the Lumbar Spine", Operative Techniques in Orthopaedics, 7 (1):27-35 (1997).
Greenblatt, et. al., "Needle Nerve Stimulator-Locator", 41 (5):599-602 (1962).
H.M. Mayer, "Minimally Invasive Spine Surgery, A Surgical Manual", Chapter 12, pp. 117-131 (2000).
Hinrichs, et al., "A trend-detection algorithm for intraoperative EEG monitoring", Med. Eng. Phys. 18 (8):626-631 (1996).
Bergey et al., "Endoscopic Lateral Transpsoas Approach to the Lumbar Spine", Spine 29 (15):1681-1688 (2004).
Holland, "Spine Update, Intraoperative Electromyography During Thoracolumbar Spinal Surgery", 23 (17):1915-1922 (1998).
Holland, et al., "Continuous Electromyographic Monitoring to Detect Nerve Root Injury During Thoracolumbar Scoliosis Surgery", 22 (21):2547-2550 (1997), Lippincott-Raven Publishers.
Hovey, A Guide to Motor Nerve Monitoring, pp. 1-31, Mar. 20, 1998, The Magstim Company Limited.
Kevin T. Foley, et. al., "Microendoscipic Discectomy" Techniques in Neurosurgery, 3:(4):301-307, © 1997 Lippincott-Raven Publishers, Philadelphia.
Kossmann et al., "The use of a retractor system (SynFrame) for open, minimal invasive reconstruction of the anterior column of the thoracic and lumbar spine", 10:396-402 (2001).
Kossmann, et. al., "Minimally Invasive Vertebral Replacement with Cages in Thoracic and Lumbar Spine", European Journal of Trauma, 2001, No. 6, pp. 292-300.
Lenke, et. al., "Triggered Electromyographic Threshold for Accuracy of Pedicle Screw Placement, An Animal Model and Clinical Correlation", 20 (14):1585-1591 (1995).
Lomanto et al., "7th World Congress of Endoscopic Surgery" Singapore, Jun. 1-4, 2000 Monduzzi Editore S.p.A.; email: monduzzi@monduzzi.com, pp. 97-103 and 105-111.
MaGuire, et. al., "Evaluation of Intrapedicular Screw Position Using Intraoperative Evoked Electromyography", 20 (9):1068-1074 (1995).
Mathews et al., "Laparoscopic Discectomy With Anterior Lumbar Interbody Fusion, A Preliminary Review", 20 (16):1797-1802, (1995), Lippincott-Raven Publishers.
Bertagnoli, et. al., "The AnteroLateral transPsoatic Approach (ALPA), A New Technique for Implanting Prosthetic Disc-Nucleus Devices", 16 (4):398-404 (2003).
Michael R. Isley, et. al., "Recent Advances in Intraoperative Neuromonitoring of Spinal Cord Function: Pedicle Screw Stimulation Techniques", Am. J. End Technol. 37:93-126 (1997).
Minahan, et. al., "The Effect of Neuromuscular Blockade on Pedicle Screw Stimulation Thresholds" 25(19):2526-2530 (2000).
Pimenta et. al., "Implante de prótese de núcleo pulposo: análise inicial", J Bras Neurocirurg 12 (2):93-96, (2001).
Raymond J. Gardocki, MD, "Tubular diskectomy minimizes collateral damage", AAOS Now, Sep. 2009 Issue, http://www.aaos.org/news/aaosnow/sep09/clinical12.asp.
Raymond, et. al., "The NerveSeeker: A System for Automated Nerve Localization", Regional Anesthesia 17:151-162 (1992).
Reidy, et. al., "Evaluation of electromyographic monitoring during insertion of thoracic pedicle screws", British Editorial Society of Bone and Joint Surgery 83 (7):1009-1014, (2001).
Rose et al., "Persistently Electrified Pedicle Stimulation Instruments in Spinal Instrumentation: Technique and Protocol Development", Spine: 22(3): 334-343 (1997).
Teresa Riordan "Patents; A businessman invents a device to give laparoscopic surgeons a better view of their work", New York Times www.nytimes.com/2004/29/business/patents-businessman-invents-device-give-la (Mar. 2004).
Toleikis, et. al., "The usefulness of Electrical Stimulation for Assessing Pedicle Screw Placements", Journal of Spinal Disorders, 13 (4):283-289 (2000).
U.Schick, et. al., "Microendoscopic lumbar discectomy versus open surgery: an intraoperative EMG study", pp. 20-26, Published online: Jul. 31, 2001 © Springer-Verlag 2001.
Bose, et. al., "Neurophysiologic Monitoring of Spinal Nerve Root Function During Instrumented Posterior Lumbar Spine Surgery", 27 (13):1440-1450 (2002).
Vaccaro, et. al., "Principles and Practice of Spine Surgery", Mosby, Inc. © 2003, Chapter 21, pp. 275-281.
Vincent C. Traynelis, "Spinal arthroplasty", Neurosurg Focus 13 (2):1-7. Article 10, (2002).
Welch, et. al., "Evaluation with evoked and spontaneous electromyography during lumbar instrumentation: a prospective study", J Neurosurg 87:397-402, (1997).
Zouridakis, et. al., "A Concise Guide to Intraoperative Monitoring", Library of Congress card No. 00-046750, Chapter 3, p. 21, chapter 4, p. 58 and chapter 7 pp. 119-120.
Medtronic, "Nerve Integrity Monitor, Intraoperative EMG Monitor, User's Guide", Medtronic Xomed U.K. Ltd., Unit 5, West Point Row, Great Park Road, Almondsbury, Bristol B5324QG, England, pp. 1-39.
Chapter 9, "Root Finding and Nonlinear Sets of Equations", Chapter 9:350-354, http://www.nr.com.
Digitimer Ltd., 37 Hydeway, Welwyn Garden City, Hertfordshire. AL7 3BE England, email:sales@digitimer.com, website: www.digitimer.com, "Constant Current High Voltage Stimulator, Model DS7A, For Percutaneous Stimulation of Nerve and Muscle Tissue".
Ford et al., Electrical characteristics of peripheral nerve stimulators, implications for nerve localization, Dept. of Anesthesia, University of Cincinnati College of Medicine, Cincinnati, OH 45267, pp. 73-77.
Deletis et al, "The role of intraoperative neurophysiology in the protection or documentation of surgically induced injury to the spinal cord", Correspondence Address: Hyman Newman Institute for Neurology & Neurosurgery, Beth Israel Medical Center, 170 East End Ave., Room 311, NY 10128.
Urmey "Using the nerve stimulator for peripheral or plexus nerve blocks" Minerva Anesthesiology 2006; 72:467-71.
Butterworth et. al., "Effects of Halothane and Enflurane on Firing Threshold of Frog Myelinated Axon", Journal of Physiology 411:493-516, (1989) From the Anesthesia Research Labs, Brigham and Women's Hospital, Harvard Medical School, 75 Francis St., Boston, MA 02115, jp.physoc.org.
Calancie, et. al., "Threshold-level multipulse transcranial electrical stimulation of motor cortex for intraoperative monitoring of spinal motor tracts: description of method and comparison to somatosensory evoked potential monitoring" J Neurosurg 88:457-470 (1998).
Calancie, et. al., "Threshold-level repetitive transcranial electrical stimulation for intraoperative monitoring of central motor conduction", J. Neurosurg 95:161-168 (2001).
Calancie, et. al., Stimulus-Evoked EMG Monitoring During Transpedicular Lumbosacral Spine Instrumentation, Initial Clinical Results, 19 (24):2780-2786 (1994).
Carl T. Brighton, "Clinical Orthopaedics and Related Research", Clinical Orthopaedics and related research No. 384, pp. 82-100 (2001).
International Search Report for PCT/US2019/063793, Feb. 19, 2020.
International Search Report for PCT/US2017/062559, Jan. 26, 2018.
Brainstorm Website, http://neuroimage.usc.edu/brainstorm/ accessed online Oct. 9, 2021, available online Apr. 11, 2018. (Year: 2018).
Compumedics Website, "Compumedics Profusion EEG 4" accessed online Oct. 9, 2021, available online Feb. 23, 2017 (ttps://www.compumedics.com.au/wp-content/uploads/2016/08/AD125-02-Profusion-EEG4-brochureLR.pdf (Year:2017).
Intelimed Website, "Compumedics Profusion EEG 5 Top Features" accessed online Oct. 9, 2021, available online Sep. 30, 2014 2014).
Deff Corporation, No more confusion about which direction to plug in. A USB cable that can be plugged in both ways is now available. A connector is equipped with an LED indicator to check a charging

(56) References Cited

OTHER PUBLICATIONS status of a smartphone. Nov. 6, 2015 (Dec. 28, 2021 Search) Internet URL:https://deff.co.jp/news/dca-mbled (Document showing known technology).
"Long, S; "Phase Locked Loop Circuits", Apr. 27, 2005". (Year: 2005).
Brainstorm website, https://web.archive.org/web/20180421074035/https://neuroimage.usc.edu/brainstorm/Tutorials/MontageEditor, available online Apr. 21, 2018 (Year: 2018).
Brainstorm website, https://web.archive.org/web/20180330235454/http://neuroimage.usc.edu/brainstorm/Tutorials/CreateProtocol,) available on Mar. 30, 2018 (Year: 2018).
Brainstorm website,https://web.archive.org/web/20180416072211/http://neuroimage.usc.edu/brainstorm/Screenshots , available on Apr. 16, 2018 (Year: 2018).
Brainstorm website,https://web.archive.org/web/20180505021718/https://neuroimage.usc.edu/brainstorm/Tutorials/Epileptogenicity, available on May 5, 2018 (Year: 2018).

* cited by examiner
† cited by third party

SYSTEMS AND METHODS OF SYNCHRONIZING EEG DATA WITH A PATIENT'S ASSOCIATED AUDIO AND VIDEO DATA

CROSS-REFERENCE

The present specification relies on U.S. Provisional Patent Application No. 63/492,893, titled "Systems and Methods of Synchronizing EEG Data with a Patient's Associated Audio and Video Data", filed on Mar. 29, 2023, for priority, the entirety of which is herein incorporated by reference in its entirety.

FIELD

The present specification is related generally to the field of neurophysiological monitoring. More specifically, the present specification is related to systems and methods for synchronizing EEG data with a patient's associated audio and video over an extended period of time.

BACKGROUND

In diagnosing epilepsy using EEG (Electroencephalography) recordings, it is frequently beneficial to simultaneously record the audio and video of a patient. There are many reasons for this, including EEG quality assessment and collecting diagnostic information. Specifically, for EEG quality assessment, the use of video and audio data enables the differentiation of true EEG activity from artifacts. For instance, a chewing activity may create seizure-like EEG activity, when in fact, it is not a seizure.

Diagnostic information, or being able to study the patient's behavior before, during, and after a seizure may help classify as well as localize the seizure. For example, if the seizure starts with moving the fingers of the left hand, the corresponding part of the motor cortex is suspected to be involved in the seizure. In pseudo seizures (psychosomatic seizures), the seizure may be seen on video, but not the EEG. Audio and/or video may also be used to validate an EEG. If the recorded video seizure activity before the EEG signal, it may be concluded that the recorded EEG is not reflecting the source of the start of the seizure but represents secondary activation.

For at least the above reasons, it is imperative to be able to accurately and tightly synchronize and correlate the EEG data, video data, and audio data. However, the EEG, the video, and the audio data streams of the patient are frequently created separately and combined using EEG software implemented by a computer. Consequently, each data stream may have different delays introduced before reaching the computer and ultimately, the EEG software.

There is often no time information integrated into the audio and video data streams of the patient, and even if there is integrated clock information, the drift in time over the duration of a recording, that can span over multiple days, is much larger than is clinically acceptable.

Accordingly, there is a need for systems and methods to enable accurate synchronization and/or correlation of EEG, audio and video data streams of a patient recorded over an extended period of time.

SUMMARY

The following embodiments and aspects thereof are described and illustrated in conjunction with systems, tools and methods, which are meant to be exemplary and illustrative, and not limiting in scope. The present application discloses numerous embodiments.

In some embodiments, the present specification describes a method of enabling synchronization of a patient's EEG data with associated video and audio data for analysis in a computing device, wherein the patient's EEG, video and audio data are acquired over a period of time of monitoring the patient, comprising: acquiring, using a plurality of sensors positioned on the patient's scalp, the EEG data of the patient; generating, using a device, first data indicative of a first differential electrical signal, second data indicative of a second differential electrical signal, a plurality of visible light signals and a plurality of audio signals, wherein the first data, the second data, the plurality of visible light signals and the plurality of audio signals are generated synchronously; receiving, by a multi-channel amplifier, the first data and second data from the device and the EEG data of the patient from the plurality of sensors; acquiring, by a video acquisition device, the plurality of visible light signals; generating, by the video acquisition device, the patient's video data and third data based on the plurality of visible light signals; acquiring, by an audio acquisition device, the plurality of audio signals; generating, by the audio acquisition device, the patient's audio data and fourth data based on the plurality of audio signals; receiving, by the computing device, the first data, the second data and the patient's EEG data from the multi-channel amplifier, the third data and the patient's video data from the video acquisition device and the fourth data and the patient's audio data from the audio acquisition device; comparing, by the computing device, the first data with the third data in order to calculate a first time compensation; comparing, by the computing device, the second data with the fourth data in order to calculate a second time compensation; and applying, by the computing device, the first time compensation to the patient's video data and the second time compensation to the patient's audio data.

Optionally, each of the first, second, third and fourth data is encoded with a predefined unique pattern of a plurality of pulses. Optionally, each of the plurality of pulses has an associated start time, end time and duration time.

Optionally, the first and third data are determined to be out of sync with each other if a start time of a pulse in the first data is different from a start time of a corresponding pulse in the third data. Optionally, the first time compensation is calculated as a difference between the start time of the pulse in the first data and the start time of the corresponding pulse in the third data.

Optionally, the second and fourth data are determined to be out of sync with each other if a start time of a pulse in the second data is different from a start time of a corresponding pulse in the fourth data. Optionally, the second time compensation is calculated as a difference between the start time of the pulse in the second data and the start time of the corresponding pulse in the fourth data.

Optionally, the predefined unique pattern has a total time duration. Optionally, the predefined unique pattern of said total time duration is repeated continuously over at least the period of time of monitoring the patient. Optionally, the predefined unique pattern includes a first stream of pulses that is followed by a second stream of pulses and that is followed by a third stream of pulses. Optionally, the first stream includes a first number of single pulses that are spaced apart from each other by a first time interval, and wherein the first stream has a first time duration. Optionally, the second stream includes a second number of dual pulses that are spaced apart from each other by a second time interval, and wherein the second stream has a second time duration. Optionally, the third stream includes a third number of triple pulses that are spaced apart from each other by a third time interval, and wherein the third stream has a third time duration. Optionally, the total time duration is a sum of the first, second and third time durations.

Optionally, the device includes at least one light emitting diode for generating the plurality of visible light signals and an acoustic generator for generating the plurality of audio signals.

Optionally, each of the first and second differential signals has a frequency ranging from 20 Hz to 40 Hz and an amplitude of 1 mV.

Optionally, the first data is compared with the third data in order to calculate a first time compensation if the first and third data are determined be out of sync with each other.

Optionally, the second data is compared with the fourth data in order to calculate a second time compensation if the second and fourth data are determined be out of sync with each other.

In some embodiments, the present specification describes a system of enabling synchronization of a patient's EEG data with associated video and audio data for analysis in a computing device, wherein the patient's EEG, video and audio data are acquired over a period of time of monitoring the patient, comprising: a plurality of sensors positioned on the patient's scalp configured to acquire the EEG data of the patient; a device configured to generate first data indicative of a first differential electrical signal, second data indicative of a second differential electrical signal, a plurality of visible light signals and a plurality of audio signals, wherein the first data, the second data, the plurality of visible light signals and the plurality of audio signals are generated mutually synchronously; a multi-channel amplifier configured to receive the first data and second data from the device and the EEG data of the patient from the plurality of sensors; a video acquisition device configured to acquire the plurality of visible light signals, wherein the video acquisition device generates the patient's video data and third data based on the plurality of visible light signals; an audio acquisition device configured to acquire the plurality of audio signals, wherein the audio acquisition device generates the patient's audio data and fourth data based on the plurality of audio signals; and one or more processors in the computing device, said one or more processors configured to execute a plurality of executable programmatic instructions to: receive the first data, the second data and the patient's EEG data from the multi-channel amplifier, the third data and the patient's video data from the video acquisition device along with the fourth data and the patient's audio data from the audio acquisition device; compare the first data with the third data in order to calculate a first time compensation if the first and third data are determined be out of sync with each other; compare the second data with the fourth data in order to calculate a second time compensation if the second and fourth data are determined be out of sync with each other; and apply the first time compensation to the patient's video data and the second time compensation to the patient's audio data.

Optionally, each of the first, second, third and fourth data is encoded with a predefined unique pattern of a plurality of pulses. Optionally, each of the plurality of pulses has an associated start time, end time and duration time. Optionally, the first and third data are determined to be out of sync with each other if a start time of a pulse in the first data is different from a start time of a corresponding pulse in the third data. Optionally, the first time compensation is calculated as a difference between the start time of the pulse in the first data and the start time of the corresponding pulse in the third data. Optionally, the second and fourth data are determined to be out of sync with each other if a start time of a pulse in the second data is different from a start time of a corresponding pulse in the fourth data. Optionally, the second time compensation is calculated as a difference between the start time of the pulse in the second data and the start time of the corresponding pulse in the fourth data. Optionally, the predefined unique pattern has a total time duration. Optionally, the predefined unique pattern of said total time duration is repeated continuously over at least the period of time of monitoring the patient.

Optionally, the predefined unique pattern includes a first stream of pulses that is followed by a second stream of pulses and that is followed by a third stream of pulses. Optionally, the first stream includes a first number of single pulses that are spaced apart from each other by a first time interval, and wherein the first stream has a first time duration. Optionally, the second stream includes a second number of dual pulses that are spaced apart from each other by a second time interval, and wherein the second stream has a second time duration. Optionally, the third stream includes a third number of triple pulses that are spaced apart from each other by a third time interval, and wherein the third stream has a third time duration. Optionally, the total time duration is a sum of the first, second and third time durations.

Optionally, the device includes at least one light emitting diode for generating the plurality of visible light signals and an acoustic generator for generating the plurality of audio signals.

Optionally, each of the first and second differential signals has a frequency ranging from 20 Hz to 40 Hz and an amplitude of 1 mV.

In some embodiments, the present specification describes a system of enabling synchronization of a patient's EEG data with associated video and audio data for analysis in a computing device, wherein the patient's EEG, video and audio data are acquired over a period of time of monitoring the patient, comprising: a plurality of sensors positioned on the patient's scalp configured to acquire the EEG data of the patient; a device configured to generate first data indicative of a first differential electrical signal, second data indicative of a second differential electrical signal, a plurality of visible light signals and a plurality of audio signals, wherein the first data, the second data, the plurality of visible light signals and the plurality of audio signals are generated mutually synchronously; a multi-channel amplifier configured to receive the first data and second data from the device and the EEG data of the patient from the plurality of sensors; a video acquisition device configured to acquire the plurality of visible light signals, wherein the video acquisition device generates the patient's video data and third data based on the plurality of visible light signals; an audio acquisition device configured to acquire the plurality of audio signals, wherein the audio acquisition device generates the patient's audio data and fourth data based on the plurality of audio signals, and wherein each of the first, second, third and fourth data is encoded with a predefined unique pattern of a plurality of pulses; and one or more processors in the computing device, said one or more processors configured to execute a plurality of executable programmatic instructions to: receive the first data, the second data and the patient's EEG data from the multi-channel amplifier, the third data and the patient's video data from the video acquisition device along with the fourth data and the patient's audio data from the audio acquisition device; compare the first data with the third data in order to calculate a first time compensation if the first and third data are determined be out of sync with each other, wherein the first and third data are determined to be out of sync with each other if a start time of a pulse in the first data is different from a start time of a corresponding pulse in the third data, and wherein the first time compensation is calculated as a difference between the start time of the pulse in the first data and the start time of the corresponding pulse in the third data; compare the second data with the fourth data in order to calculate a second time compensation if the second and fourth data are determined be out of sync with each other, wherein the second and fourth data are determined to be out of sync with each other if a start time of a pulse in the second data is different from a start time of a corresponding pulse in the fourth data, and wherein the second time compensation is calculated as a difference between the start time of the pulse in the second data and the start time of the corresponding pulse in the fourth data; and apply the first time compensation to the patient's video data and the second time compensation to the patient's audio data.

Optionally, the predefined unique pattern has a total time duration, and wherein the predefined unique pattern of said total time duration is repeated continuously over at least the period of time of monitoring the patient. Optionally, the predefined unique pattern includes a first stream of pulses that is followed by a second stream of pulses and that is followed by a third stream of pulses. Optionally, the first stream includes a first number of single pulses that are spaced apart from each other by a first time interval, and wherein the first stream has a first time duration. Optionally, the second stream includes a second number of dual pulses that are spaced apart from each other by a second time interval, and wherein the second stream has a second time duration. Optionally, the third stream includes a third number of triple pulses that are spaced apart from each other by a third time interval, and wherein the third stream has a third time duration. Optionally, the total time duration is a sum of the first, second and third time durations.

Optionally, the device includes at least one light emitting diode for generating the plurality of visible light signals and an acoustic generator for generating the plurality of audio signals.

The aforementioned and other embodiments of the present specification shall be described in greater depth in the drawings and detailed description provided below.

BRIEF DESCRIPTION OF THE DRAWINGS

The accompanying drawings illustrate various embodiments of systems, methods, and embodiments of various other aspects of the disclosure. Any person with ordinary skills in the art will appreciate that the illustrated element boundaries (e.g., boxes, groups of boxes, or other shapes) in the figures represent one example of the boundaries. It may be that in some examples one element may be designed as multiple elements or that multiple elements may be designed as one element. In some examples, an element shown as an internal component of one element may be implemented as an external component in another and vice versa. Furthermore, elements may not be drawn to scale. Non-limiting and non-exhaustive descriptions are described with reference to the following drawings. The components in the figures are not necessarily to scale, emphasis instead being placed upon illustrating principles.

DETAILED DESCRIPTION

Figure 1:
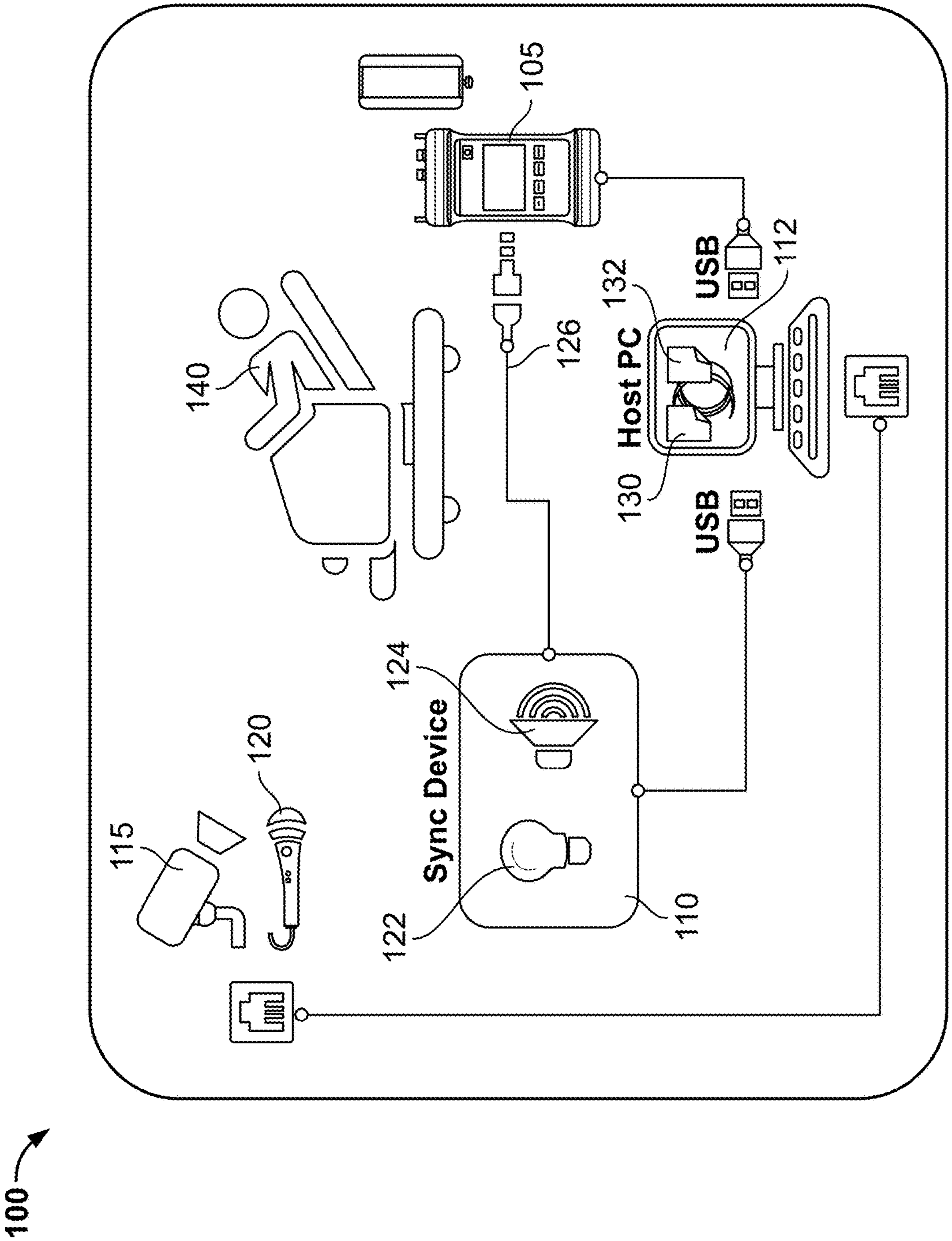
FIG. 1 illustrates an electroencephalography (EEG) system 100 configured for synchronizing detected EEG data with associated audio and video data of a patient, in accordance with some embodiments of the present specification.

The present specification is directed towards systems and methods for synchronization of EEG data, video data, and audio data. Because there is often no time information integrated into the audio and video data streams of the patient, the time drift over the duration of a recording, that can span over multiple days, is much larger than is clinically acceptable. Thus, the systems and methods of the present specification are used to allow for accurate synchronization and/or correlation of EEG data, audio data, and video data streams of a patient recorded over an extended period of time. The methods of the present specification are employed to apply a first compensation time to the patient's video data and a second compensation time to the patient's audio data in order to synchronize the patient's EEG data with the video data and audio data of the patient. In embodiments, the first compensation time may be indicative of a drift (lead or delay/lag) in time of the patient's video data with respect to the patient's EEG data. In embodiments, the second compensation time may be indicative of a drift (lead or delay/lag) in time of the patient's audio data with respect to the patient's EEG data.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In various embodiments, a computing device includes an input/output controller, at least one communications interface, and a system memory. The system memory includes at least one random access memory (RAM) and at least one read-only memory (ROM). These elements are in communication with a central processing unit (CPU) to enable operation of the computing device. In various embodiments, the computing device may be a conventional standalone computer or alternatively, the functions of the computing device may be distributed across multiple computer systems and architectures.

In some embodiments, execution of a plurality of sequences of programmatic instructions or code enable or cause the CPU of the computing device to perform various functions and processes. In alternate embodiments, hard-wired circuitry may be used in place of, or in combination with, software instructions for implementation of the processes of systems and methods described in this application. Thus, the systems and methods described are not limited to any specific combination of hardware and software.

The term "module", "application" or "engine" used in this disclosure may refer to computer logic utilized to provide a desired functionality, service or operation by programming or controlling a general purpose processor. Stated differently, in some embodiments, a module, application or engine implements a plurality of instructions or programmatic code to cause a general purpose processor to perform one or more functions. In various embodiments, a module, application or engine can be implemented in hardware, firmware, software or any combination thereof. The module, application or engine may be interchangeably used with unit, logic, logical block, component, or circuit, for example. The module, application or engine may be the minimum unit, or part thereof, which performs one or more particular functions.

In the description and claims of the application, each of the words "comprise", "include", "have", "contain", and forms thereof, are not necessarily limited to members in a list with which the words may be associated. Thus, they are intended to be equivalent in meaning and be open-ended in that an item or items following any one of these words is not meant to be an exhaustive listing of such item or items, or meant to be limited to only the listed item or items. It should be noted herein that any feature or component described in association with a specific embodiment may be used and implemented with any other embodiment unless clearly indicated otherwise.

It must also be noted that as used herein and in the appended claims, the singular forms "a," "an," and "the" include plural references unless the context dictates otherwise. Although any systems and methods similar or equivalent to those described herein can be used in the practice or testing of embodiments of the present disclosure, the preferred, systems and methods are now described.

Overview

FIG. 1 illustrates an electroencephalography (EEG) system 100 configured for synchronizing detected EEG data with associated audio and video data of a patient, in accordance with some embodiments of the present specification. The system 100 comprises a multi-channel EEG amplifier 105 in data communication with a synchronization device 110 over a first communication link 126. In addition, the EEG amplifier 105 is in data communication with a computing device 112 over a second communication link. Further, the EEG amplifier 105 is in data communication, over a third communication link, with a plurality of EEG sensors or electrodes spatially positioned on a layer of tissue such as the scalp of a patient 140. In turn, the computing device 112 is in data communication with the synchronization device 110 over a fourth communication link, a video acquisition device 115 such as a camera over a fifth communication link, and an audio acquisition device 120 such as a microphone over a sixth communication link. In some embodiments, instead of a separate video acquisition device 115 for the acquisition of video and a separate audio acquisition device 120 for the acquisition of audio, the system 100 may use a single device, such as, for example, a camera, for acquisition of both audio and video. In embodiments, the audio data stream may be captured by a microphone integrated into the video camera or a separate microphone.

It should be noted herein that each form of data is recorded into discrete data channels. For example, when a video camera is recording video data and audio data, the discrete portions of data or data sets are recorded into different channels (or streams of data). The systems and methods of the present specification contemplate synchronization of any and/or all of the data sets and/or streams with each other, therefore, any and all audio streams may be synchronized with the video data and EEG data streams using the synchronization device 110. In various embodiments, the first, second, third, fourth, fifth and sixth and any other communication links may be wired or wireless links.

It should also be noted herein that any of the data sets described throughout this specification can be evaluated absolutely (or relative to any other data set) to determine a degree of time lag and a time compensation factor to make up for the lag and that time compensation factor can then be applied to any other data set absolutely (or relative to any other data set) to synchronize the other data set with the first data set.

The plurality of EEG sensors or electrodes record electrical signals (EEG signals) from the patient's brain and communicate the analog signals to the multi-channel amplifier 105 that is configured to amplify the signals, convert the signals from an analog EEG signal to digital EEG data, and communicate the resultant digital EEG data to the computing device 112. Simultaneously, the video acquisition device 115 records video data of the patient 140 and the audio acquisition device 120 records audio data of the patient 140. The recorded video and audio data of the patient 140 are communicated to the computing device 112.

In some embodiments, the computing device 112 is configured to implement an EEG module, engine, or application 130 and a data synchronization analysis (DSA) module, engine, or application 132. In some embodiments, the EEG module 130 and DSA module 132 are configured to receive, synchronize and combine the EEG data, video data and audio data of the patient 140 for further processing, analyses and display on a monitor or display screen associated with the computing device 112.

Synchronization Device 110

In accordance with aspects of the present specification, the synchronization device 110 is configured to generate, synchronously, a first event, a second event, and a third event. That is, the first event, second event, and third event are generated simultaneously and therefore have the same start times.

The first event corresponds to generation of first data to be used for video synchronization and second data to be used for audio synchronization. In some embodiments, the first data is indicative of a first differential electrical signal and the second data is indicative of a second differential electrical signal. The first data and second data are received by the multi-channel amplifier 105 (via the first communication link 126) and digitized by the multi-channel amplifier 105. The first data and second data, along with the EEG data of the patient, is communicated, by the multi-channel amplifier 105 to the computing device 112. In some embodiments, the first differential electrical signal and second differential electrical signal have a frequency in a range of 20 Hz to 40 Hz and an amplitude in a range of 0.5 mV to 2.5 mV and preferably of 1 mV. In some embodiments, the synchronization device 110 includes at least one electrical circuit component for generating the first data and second data.

In some embodiments, if the audio and video streams are synchronous, for instance when the audio or sound is recorded directly by the camera 115 (to generate combined audio and video stream), then the EEG and video synchronization is enabled by using the audio signal, in the combined audio and video stream, for synchronization since it is sampled with a much higher frequency (kHz instead of Hz) compared to the video recording, thereby, allowing for a more accurate synchronization.

The second event corresponds to generation of a plurality of visible light signals. In some embodiments, the plurality of visible light signals includes one or more blinking or pulsating visual indicators such as, for example LEDs 122 (light emitting diode). In some embodiments, infrared light is used (in order to minimize disturbing people in the vicinity) to generate a plurality of light signals in which case the video acquisition device 115 is capable of recording infrared light. The plurality of visible light signals is recorded by the video acquisition device 115 and digitized in order to generate third data indicative of the plurality of visible light signals. The video acquisition device 115 communicates the third data to the computing device 112. In some embodiments, the synchronization device 110 includes at least one LED for generating the plurality of visible light signals.

The third event corresponds to generation of a plurality of audio signals. In some embodiments, the plurality of audio signals includes a beeping or pulsating sequence of audio or sound. The plurality of audio signals is used to separately identify different instances of synchronization sounds to avoid synchronizing a wrong event with a wrong time within the EEG data. Thus, the plurality of audio signals act as a “fingerprint” to separate different sound events from one another. In some embodiments, the sound is generated by an acoustics generator and output by, for example, a speaker 124. The plurality of audio signals is recorded by the audio acquisition device 120 and digitized in order to generate fourth data indicative of the plurality of audio signals. The audio acquisition device 120 communicates the fourth data to the computing device 112. In some embodiments, the synchronization device 110 includes a speaker and acoustics generator 124 for generating the plurality of audio signals. In some embodiments, the audio or sound has a high frequency, ranging from 500 Hz to 5 kHz, to optimize synchronization and minimize disturbance from the sound.

In some embodiments, the synchronization device 110 also generates a trigger pulse or signal that is communicated to the multi-channel amplifier 105 (via the first communication link 126) either through a dedicated trigger input or using the differential amplifier inputs (similar inputs to where the patient electrodes are connected). In some embodiments, the trigger pulse or signal is generated synchronously with the first differential signal and the second differential signal corresponding to the first event. Thus, when the synchronization device 110 generates the first differential signal, the second differential signal, the plurality of visible light signals, and the plurality of audio signals it also, at the same time or simultaneously, delivers the trigger pulse or signal through the first communication link 126 to the multi-channel amplifier 105. In accordance with aspects of the present specification, the trigger pulse or signal tags the first, second, third and fourth data with a very precise point in time and marks the trigger pulse or signal with a corresponding fourth event that is displayed as a discrete point in time (for example, shown as an event 270 in FIG. 2) in the EEG data recording.

Thus, in embodiments, the first event, second event, and third event are acquired or recorded separately by the multi-channel amplifier 105, the video acquisition device 115 and the audio acquisition device 120, respectively. However, the first differential electrical signal corresponding to the first data, the second differential electrical signal corresponding to the second data, the plurality of visible light signals corresponding to the third data, and the plurality of audio signals corresponding to the fourth data are generated synchronously by the synchronization device 110. That is, the start times of each of these signals is same.

It should be appreciated that in various embodiments the synchronization device 110 may be configured to integrate the respective components for generating the first event, second event, and third event. For example, the synchronization device 110 may integrate an electrical circuit for generating the first data and second data, at least one LED for generating the plurality of visible light signals and a speaker/acoustics generator for generating the plurality of audio signals. In alternate embodiments, the respective components for generating the first data, second data, third data, and fourth data may be separate or distributed.

In some embodiments, the first data, second data, third data, and fourth data possess the following plurality of characteristics:

A) Each of the first, second, third and fourth data stream is encoded with a predefined unique pattern or sequence of pulses. The unique pattern or sequence of pulses have an overall predefined time duration of ‘T’ seconds. It should be noted that the pulses of each of the first and second data correspond to a plurality of pulses of each of the first differential electrical signal and second differential electrical signal, the pulses of the third data correspond to periodic flashes or pulsation of the visible light (that flash or pulsate in tandem with the plurality of pulses of the first and second differential electrical signals) and the pulses of the fourth data correspond to periodic beeping of the audio or sound (that beeps in tandem with the plurality of pulses of the first and second differential electrical signals). Also, in embodiments, each pulse (of the first, second, third and fourth data) has an associated start time, an end time and a time duration that are predefined.

B) The unique pattern or sequence of pulses, over the predefined time duration of ‘T’ seconds, is same and synchronous for each of the first, second, third and fourth data. Synchronous refers to a situation where, for example, each pulse of each of the first, second, third and fourth data has the same start time.

C) The unique pattern or sequence of pulses, having an overall predefined time duration of ‘T’ seconds, is repeated over an extended period of time. In some embodiments, the extended period of time corresponds to at least the period of time during which the patient’s EEG, video and audio data is recorded.

D) The unique pattern or sequence of pulses, having an overall predefined time duration of ‘T’ seconds, allows uniquely recognizing a specific synchronization event (of the first synchronization event, second synchronization event, and third synchronization event) over the extended period of time.

E) The unique pattern or sequence of pulses, having an overall predefined time duration of ‘T’ seconds, enables unique identification of the recording as well as the point in time over an extended period of time. The unique pattern or sequence of pulses enables unique identification of the recording so that the EEG recording can automatically be linked to the corresponding video and audio streams. It should be appreciated that the unique pattern or sequence of pulses convey different codes that allow the EEG module 130 and DSA module 132 (which are configured accordingly) to analyze the codes in the unique pattern or sequence of pulses in the video signal, for example, and the EEG data to detect which codes in the different data streams belongs together. For instance, in a non-limiting example, the synchronization device 110 may generate visible light signals and audio signals comprising code 1 (corresponding to a first pattern, sequence or stream of pulses), then code 2 (corresponding to a second pattern, sequence or stream of pulses), and then code 3 (corresponding to a third pattern, sequence or stream of pulses). The visible light signals and audio signals may be recorded, for example, by the camera 115 in order to generate corresponding video and audio streams and stored together with the EEG data. The EEG module 130 and DSA module 132 then analyzes, as they are configured to do so, both the EEG and video data and match the right codes or the pattern, sequence or stream of pulses to each other.

Figure 2:
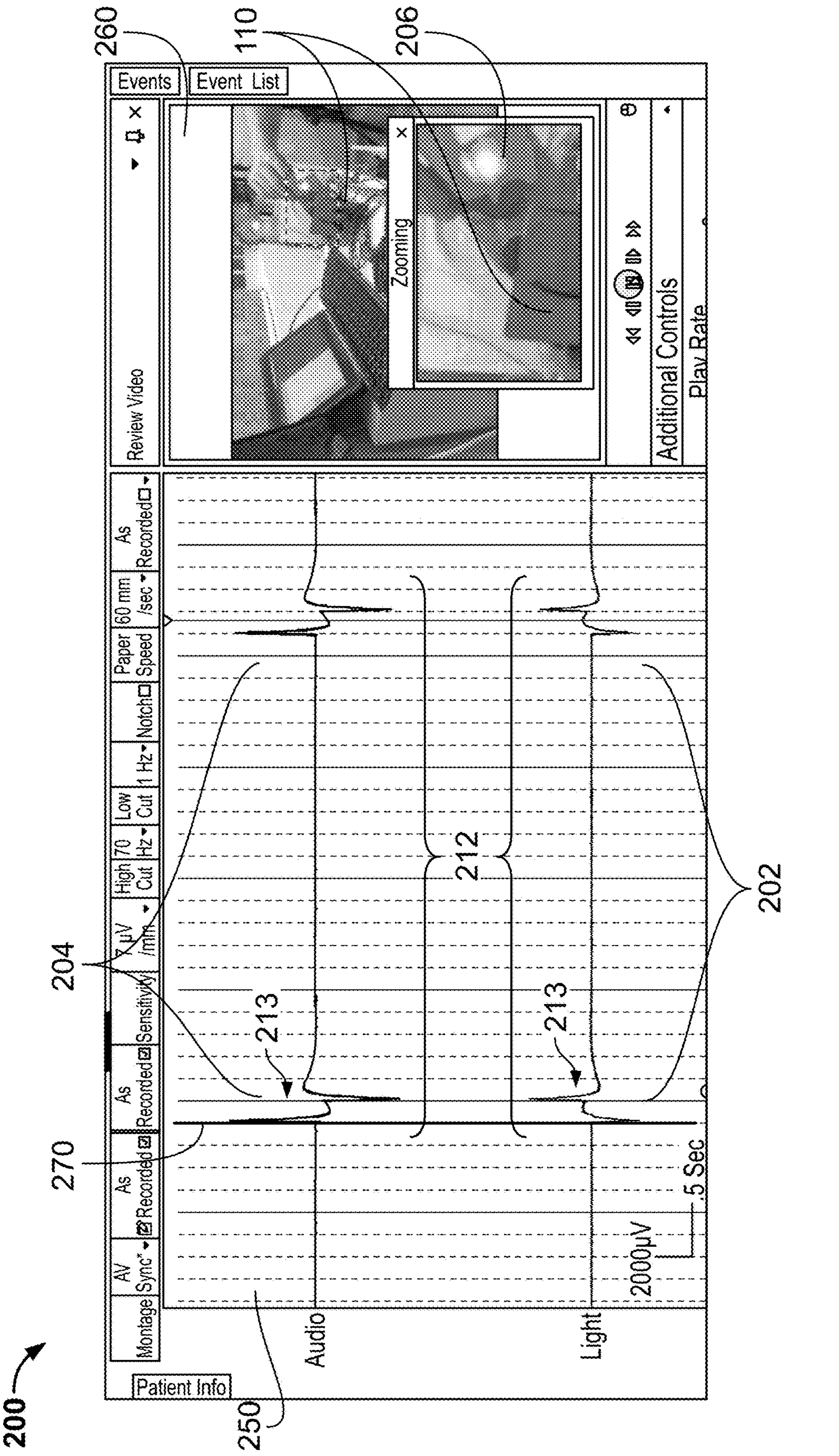
FIG. 2 is a GUI (graphical user interface) generated by EEG and DSA (Data Synchronization Analysis) modules, in accordance with some embodiments of the present specification.
Figure 2:
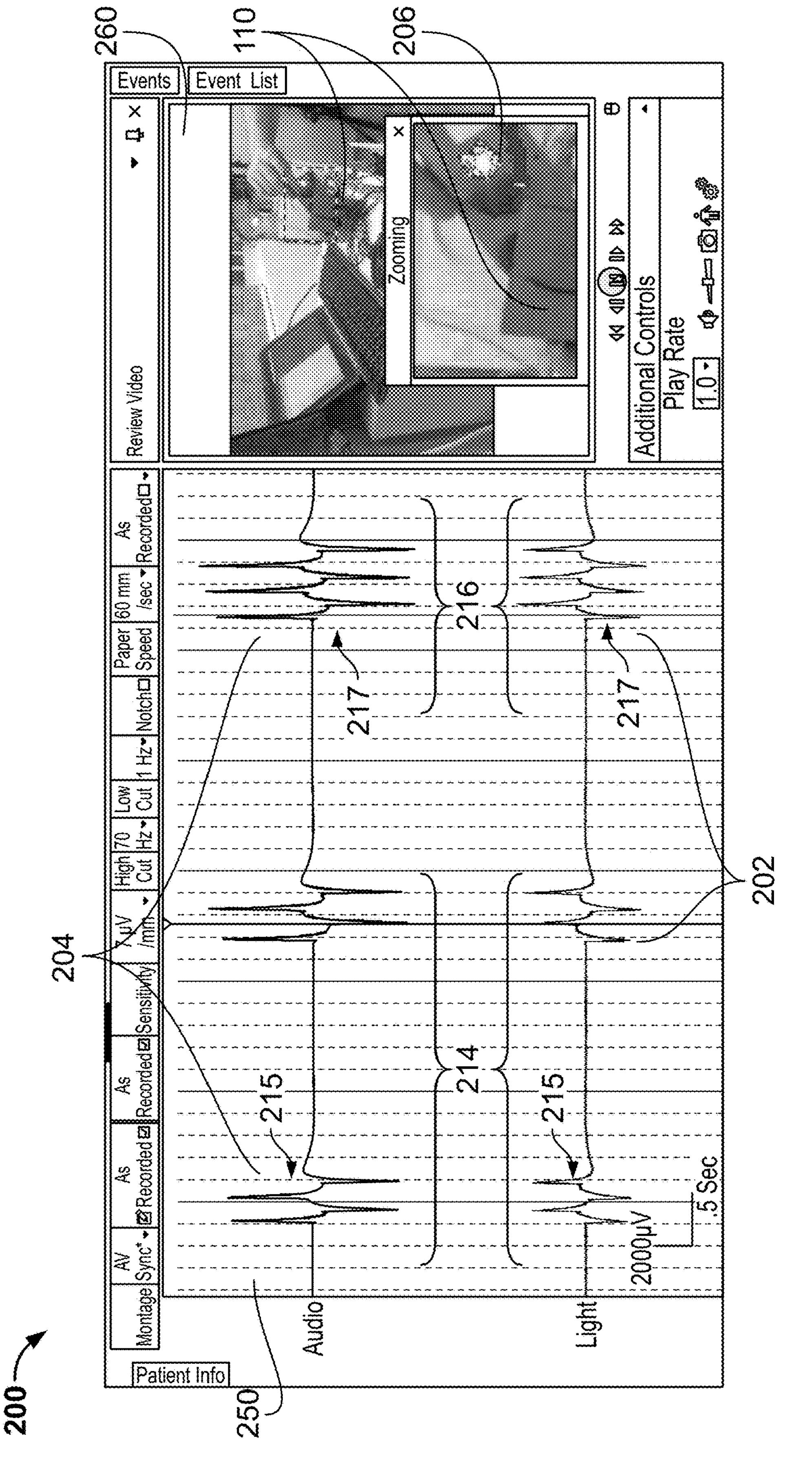

FIG. 2 is a GUI (graphical user interface) 200 generated by the EEG and DSA modules 130, 132 (FIG. 1), in accordance with some embodiments of the present specification. As shown, the GUI 200 has a first area or window 250 that displays graphical illustrations of first data 202 indicative of a plurality of pulses of the first differential electrical signal that are used for video synchronization and second data 204 indicative of a plurality of pulses of the second differential electrical signal that are used for audio synchronization. A second window 260 displays the synchronization device 110 (the first data 202 and second data 204 which are also generated by the synchronization device 110) that generates third data 206 indicative of a plurality of visible light signals and fourth data indicative of a plurality of audio signals. Additionally, the synchronization device 110 generates the trigger pulse or signal (synchronously with the first and second differential electrical signals) that corresponds to the fourth event 270. The trigger pulse or signal along with the first, second, third and fourth data are synchronous at the time of generation.

In embodiments, each of the first, second, third and fourth data is encoded with a predefined unique pattern or sequence of pulses having an overall predefined time duration of ‘T’ seconds. In various embodiments, the predefined unique pattern or sequence of pulses includes a plurality of streams of pulses wherein each of the plurality of streams has a predefined time duration and includes a predefined number and type of pulses. Each of the pulses, for each of the first, second, third and fourth data, is synchronous at the time of generation. Stated differently, a start time of each corresponding pulse is same for each of the first, second, third and fourth data.

In one non-limiting embodiment, the predefined unique pattern or sequence of pulses includes a first stream of pulses 212 that is followed by a second stream of pulses 214, which, in turn, is followed by a third stream of pulses 216. The first stream 212 includes ‘p’ number of singular pulses 213 that are spaced apart from each other by a predefined time interval. The first stream 212 has a total time duration Tp. The second stream 214 includes ‘q’ number of dual pulse sets 215 (that is, two pulses generated in quick succession) such that the dual pulse sets are spaced apart from each other by a predefined time interval. The second stream 214 has a total time duration Tq. The third stream 216 includes ‘r’ number of triple pulse sets 217 (that is, three pulses generated in quick succession) such that the triple pulse sets are spaced apart from each other by a predefined time interval. The third stream 216 has a total time duration Tr. The overall total predefined time duration of the predefined unique pattern or sequence of pulses T=Tp+Tq+Tr.

In various embodiments, p, q and r may or may not be equal or of the same number. Similarly, in various embodiments, Tp, Tq and Tr may or may not be equal or of the same duration. It should also be appreciated that while FIG. 2 illustrates three pulse streams 212, 214, 216, in alternate embodiments, the number of streams of pulses may vary from 2 to 6 streams. Also, the sequence of the pulse streams may vary in embodiments. In various embodiments, but not limited to such embodiments, the number of pulses in each of the first, second and third stream of pulses varies from 1 to 9, each unique pattern or sequence of pulses consists of three trains or streams, time between pulses is 0.2 seconds and time between the trains or streams is 2 seconds. In one embodiment, p=4, q=2, r=3 and Tp=Tq=Tr=10 seconds. Therefore, an overall predefined time duration of the predefined unique pattern or sequence of pulses T=Tp+Tq+Tr=10+10+10=30 seconds.

In embodiments, the predefined unique pattern or sequence of pulses comprising the first pulse stream 212, the second pulse stream 214, and the third pulse stream 216 is repeated over at least a time duration for which the patient’s EEG, video and audio data is recorded.

Synchronization Method

The DSA module 132 is configured to receive and analyze the first data, second data, third data and fourth data in order to determine if the patient’s EEG data, audio data, and video data is in synchrony over a period of time during which the patient’s EEG data, video data and audio data is recorded. It should be appreciated that in some embodiments the DSA module 132 is separate from the EEG module 130. However, in alternate embodiments, the functionalities of the DSA module 132 may be integrated in the EEG module 130 itself.

Figure 3:
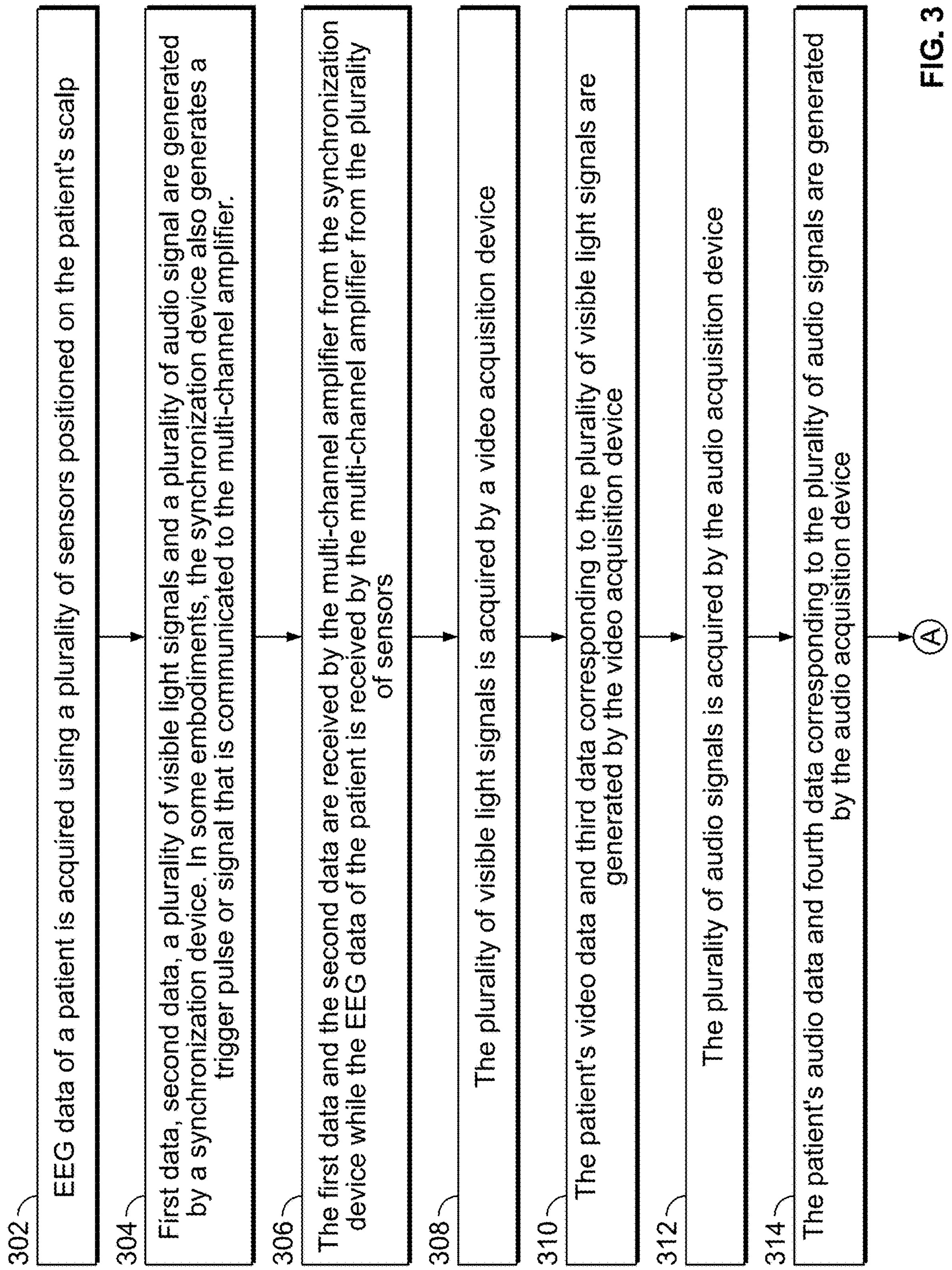
FIG. 3 is a flowchart of a plurality of exemplary steps of a method for synchronizing a patient's EEG, audio, and video data acquired over a period of time while monitoring the patient, in accordance with some embodiments of the present specification.
Figure 3:
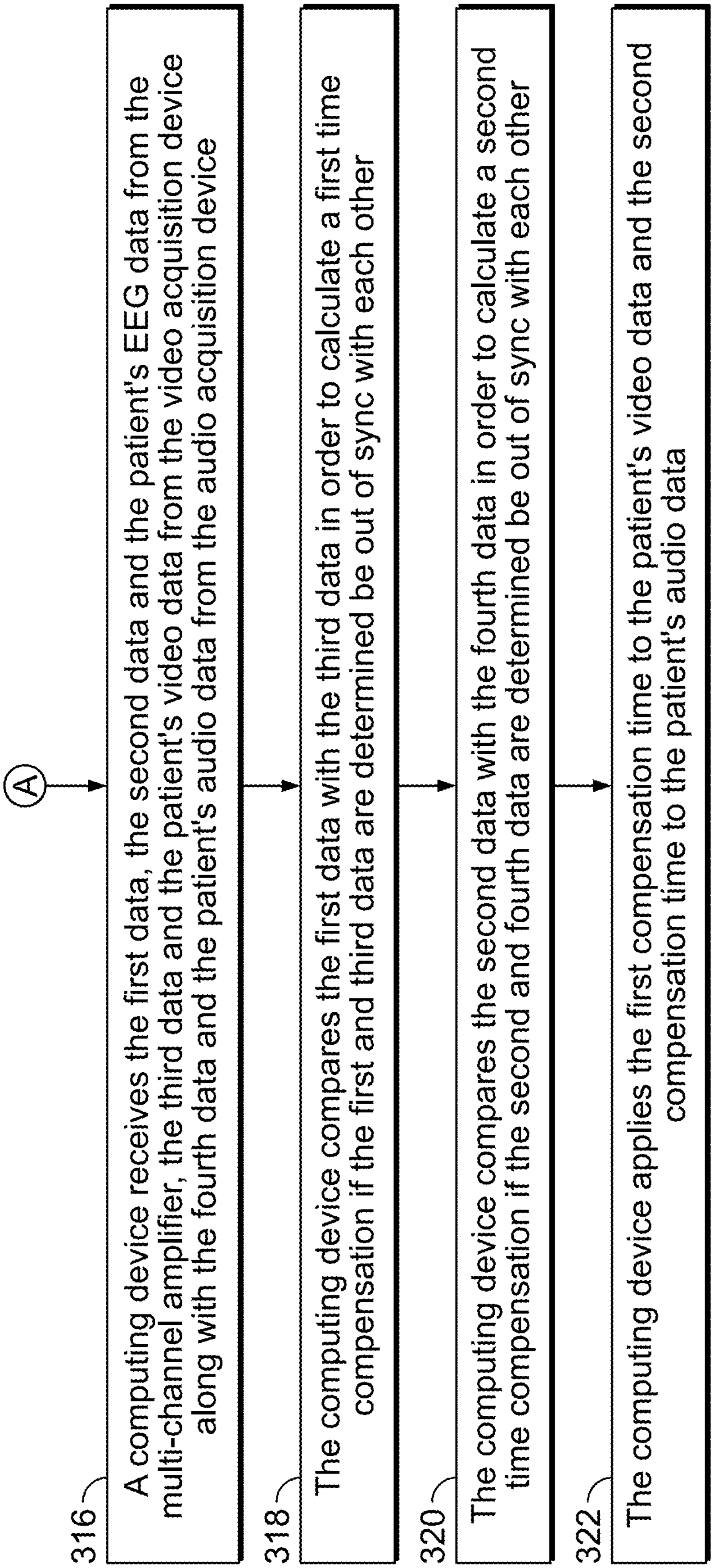

FIG. 3 is a flowchart of a plurality of exemplary steps of a method 300 of enabling synchronization of a patient’s EEG data, audio data, and video data acquired over a period of time during monitoring of a patient, in accordance with some embodiments of the present specification. In embodiments, the DSA module 132, in tandem with the EEG module 130, is configured to implement a plurality of instructions or programmatic code in order to execute the method 300.

Referring now to FIGS. 1 and 3 simultaneously, at step 302, the EEG data of the patient is acquired using a plurality of sensors positioned on the patient’s scalp.

At step 304, first data, second data, a plurality of visible light signals and a plurality of audio signals are generated by the synchronization device 110. In some embodiments, the first data is indicative of a first differential electrical signal and the second data is indicative of a second differential electrical signal. In embodiments, the first data, the second data, the plurality of visible light signals and the plurality of audio signals are generated mutually synchronously. In some embodiments, each of the first and second differential signals has a frequency ranging from 20 Hz to 40 Hz and an amplitude of 1 mV.

In some embodiments, the synchronization device also generates a trigger pulse or signal that is communicated to the multi-channel amplifier 105 (on the first communication link 126) either through a dedicated trigger input or using the differential amplifier inputs (similar inputs to where the patient electrodes are connected). In some embodiments, the trigger pulse or signal is generated synchronously with the first and second differential signals corresponding to the first event. Thus, when the synchronization device 110 generates the first differential signal, the second differential signal, the plurality of visible light signals and the plurality of audio signals it also, at the same time or simultaneously, delivers the trigger pulse or signal through the first communication link 126 to the multi-channel amplifier 105.

In some embodiments, the synchronization device 110 includes at least one light emitting diode for generating the plurality of visible light signals and an acoustic generator for generating the plurality of audio signals along with a speaker for outputting the plurality of audio signals.

At step 306, the first data and the second data are received by the multi-channel amplifier 105 from the synchronization device 110 while the EEG data of the patient is received by the multi-channel amplifier from the plurality of sensors.

At step 308, the plurality of visible light signals generated by the synchronization device 110 is acquired or received by a video acquisition device 115. At step 310, the patient's video data and the third data corresponding to the plurality of visible light signals are generated by the video acquisition device 115.

At step 312, the plurality of audio signals generated by the synchronization device 110 is acquired or received by the audio acquisition device 120. At step 314, the patient's audio data and fourth data corresponding to the plurality of audio signals are generated by the audio acquisition device 120.

In some embodiments, each of the first data, second data, third data and fourth data is encoded with a predefined unique pattern of a plurality of pulses, wherein each of the plurality of pulses has an associated start time, end time, and duration. In some embodiments, the predefined unique pattern has a total time duration. In some embodiments, the predefined unique pattern of the total time duration is repeated continuously over at least the period of time of monitoring the patient.

In some embodiments, the predefined unique pattern includes a first stream of pulses that is followed by a second stream of pulses and that is followed by a third stream of pulses. In some embodiments, the first stream includes a first number of single pulses that are spaced apart from each other by a first time interval, and has a first time duration. In some embodiments, the second stream includes a second number of dual pulses that are spaced apart from each other by a second time interval, and has a second time duration. In some embodiments, the third stream includes a third number of triple pulses that are spaced apart from each other by a third time interval, and wherein the third stream has a third time duration. In embodiments, the total time duration of the predefined unique pattern is a sum of the first time duration, second time duration, and third time durations.

At step 316, the computing device 112 receives the first data, the second data and the patient's EEG data from the multi-channel amplifier 105, the third data and the patient's video data from the video acquisition device 115 along with the fourth data and the patient's audio data from the audio acquisition device 120.

At step 318, the computing device 112 compares the first data with the third data in order to calculate a first time compensation if the first and third data are determined be out of sync with each other. In some embodiments, the first and third data are determined to be out of sync with each other (asynchronous) if a start time of a pulse in the first data is different from a start time of a corresponding pulse in the third data. In some embodiments, the first time compensation is calculated as a difference between the start time of the pulse in the first data and the start time of the corresponding pulse in the third data.

At step 320, the computing device 112 compares the second data with the fourth data in order to calculate a second time compensation if the second and fourth data are determined be out of sync with each other. In some embodiments, the second and fourth data are determined to be out of sync with each other if a start time of a pulse in the second data is different from a start time of a corresponding pulse in the fourth data. In some embodiments, the second time compensation is calculated as a difference between the start time of the pulse in the second data and the start time of the corresponding pulse in the fourth data.

In some embodiments, steps 318 and 320 are implemented at the beginning and end of the EEG monitoring, video recording, and audio recording of the patient. In some embodiments, the steps 318 and 320 are implemented additionally or alternatively on a regular basis to ensure a high degree of synchronization across the whole duration of the EEG, video and audio recording of the patient.

At step 322, the computing device 112 applies the first compensation time to the patient's video data and the second compensation time to the patient's audio data in order to synchronize the patient's EEG data with the video and audio data of the patient. It should be appreciated that the first compensation time may be indicative of a drift (lead or delay/lag) in time of the patient's video data with respect to the patient's EEG data. Also, the second compensation time may be indicative of a drift (lead or delay/lag) in time of the patient's audio data with respect to the patient's EEG data.

The above examples are merely illustrative of the many applications of the systems and methods of the present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

What is claimed is:

1. A method of enabling synchronization of a patient's EEG data with associated video and audio data for analysis in a computing device, wherein the patient's EEG, video and audio data are acquired over a period of time of monitoring the patient, comprising:

acquiring, using a plurality of sensors positioned on the patient's scalp, the EEG data of the patient;

generating, using a device, first data indicative of a first differential electrical signal, second data indicative of a second differential electrical signal, a plurality of visible light signals and a plurality of audio signals, wherein the first data, the second data, the plurality of visible light signals and the plurality of audio signals are generated synchronously, wherein the first data, the second data, the plurality of visible light signals, and the plurality of audio signals are generated simultaneously by the device and are each encoded with a same predefined repeating pattern of pulses;

receiving, by a multi-channel amplifier, the first data and second data from the device and the EEG data of the patient from the plurality of sensors;

acquiring, by a video acquisition device, the plurality of visible light signals;

generating, by the video acquisition device, the patient's video data and third data based on the plurality of visible light signals;

acquiring, by an audio acquisition device, the plurality of audio signals;

generating, by the audio acquisition device, the patient's audio data and fourth data based on the plurality of audio signals;

receiving, by the computing device, the first data, the second data and the patient's EEG data from the multi-channel amplifier, the third data and the patient's video data from the video acquisition device and the fourth data and the patient's audio data from the audio acquisition device;

comparing, by the computing device, the first data with the third data in order to calculate a first time compensation, wherein the first data is directly compared with the third data based on corresponding pulse timings of the predefined repeating pattern of pulses;

comparing, by the computing device, the second data with the fourth data in order to calculate a second time compensation, wherein the second data is directly compared with the fourth data based on corresponding pulse timings of the predefined repeating pattern of pulses; and applying, by the computing device, the first time compensation to the patient's video data and the second time compensation to the patient's audio data.

2. The method of claim 1, wherein each pulse of the predefined repeating pattern of pulses has an associated start time, end time and duration time.

3. The method of claim 2, wherein the first and third data are determined to be out of sync with each other if a start time of a pulse in the first data is different from a start time of a corresponding pulse in the third data.

4. The method of claim 3, wherein the first time compensation is calculated as a difference between the start time of the pulse in the first data and the start time of the corresponding pulse in the third data.

5. The method of claim 2, wherein the second and fourth data are determined to be out of sync with each other if a start time of a pulse in the second data is different from a start time of a corresponding pulse in the fourth data.

6. The method of claim 5, wherein the second time compensation is calculated as a difference between the start time of the pulse in the second data and the start time of the corresponding pulse in the fourth data.

7. The method of claim 1, wherein the predefined repeating pattern of pulses has a total time duration.

8. The method of claim 7, wherein the predefined repeating pattern of pulses of said total time duration is repeated continuously over at least the period of time of monitoring the patient.

9. The method of claim 7, wherein the predefined repeating pattern of pulses includes a first stream of pulses that is followed by a second stream of pulses that is followed by a third stream of pulses.

10. The method of claim 9, wherein the first stream includes a first number of single pulses that are spaced apart from each other by a first time interval, and wherein the first stream has a first time duration.

11. The method of claim 10, wherein the second stream includes a second number of dual pulses that are spaced apart from each other by a second time interval, and wherein the second stream has a second time duration.

12. The method of claim 11, wherein the third stream includes a third number of triple pulses that are spaced apart from each other by a third time interval, and wherein the third stream has a third time duration.

13. The method of claim 12, wherein the total time duration is a sum of the first, second and third time durations.

14. The method of claim 1, wherein the device includes at least one light emitting diode for generating the plurality of visible light signals and an acoustic generator for generating the plurality of audio signals.

15. The method of claim 1, wherein each of the first and second differential signals has a frequency ranging from 20 Hz to 40 Hz and an amplitude of 1 mV.

16. The method of claim 1, wherein the first data is compared with the third data in order to calculate a first time compensation if the first and third data are determined to be out of sync with each other.

17. The method of claim 1, wherein the second data is compared with the fourth data in order to calculate a second time compensation if the second and fourth data are determined to be out of sync with each other.

* * * * *